United States Patent
Shilderman et al.

(10) Patent No.: US 8,641,985 B2
(45) Date of Patent: Feb. 4, 2014

(54) CONTROL SYSTEM FOR OZONE STERILIZATION IN MULTIPLE COMPACT CHAMBERS

(75) Inventors: Yuval Shilderman, Nes Ziona (IL); Meni Perets, Dimona (IL); Uri Peiper, Ramat Hasharon (IL); Yekutiel Alper, Rishon Lezion (IL); Meir Markovich, Modiin (IL)

(73) Assignee: Tuttnauer Ltd., Bet Shemesh (IL)

( * ) Notice: Subject to any disclaimer, the term of this patent is extended or adjusted under 35 U.S.C. 154(b) by 0 days.

(21) Appl. No.: 13/217,450

(22) Filed: Aug. 25, 2011

(65) Prior Publication Data

US 2013/0052078 A1    Feb. 28, 2013

(51) Int. Cl.
*A61L 2/00* (2006.01)
*A61L 9/00* (2006.01)
*B08B 3/00* (2006.01)
*A62B 19/00* (2006.01)

(52) U.S. Cl.
USPC ........... 422/306; 422/292; 422/295; 422/305; 134/30; 134/94.1; 134/95.1; 134/95.3; 134/102.1; 128/202.25

(58) Field of Classification Search
USPC ............. 422/1, 26–28, 186.07, 292, 295, 422/305–306; 134/30, 94.1, 95.1, 95.3, 134/102.1; 128/202.25
See application file for complete search history.

(56) References Cited

U.S. PATENT DOCUMENTS

| | | | |
|---|---|---|---|
| 4,261,950 A | | 4/1981 | Bainbridge et al. |
| 5,141,722 A | * | 8/1992 | Nagashima ................... 422/292 |
| 5,556,607 A | | 9/1996 | Childers et al. |
| 5,788,925 A | * | 8/1998 | Pai et al. ............................ 422/3 |
| 2011/0008207 A1 | | 1/2011 | Arai et al. |

FOREIGN PATENT DOCUMENTS

| | | |
|---|---|---|
| CN | 201061624 | 3/2008 |
| EP | 0898971 | 3/1999 |
| JP | 1268557 | 10/1989 |
| WO | WO0066186 | 11/2000 |

* cited by examiner

*Primary Examiner* — Monzer R Chorbaji
(74) *Attorney, Agent, or Firm* — Mark M. Friedman (57) ABSTRACT

A control system for multiple sterilization chambers for the sterilization of medical and other instruments interact with a common vacuum pump, steam generator and ozone generator via a common controller. Instead of placing all instruments of one type in one large chamber and running one generic sterilization program followed by another such program, instruments may be grouped by the type of sterilization program needed and the sterilization programs may be run using a single pump and a single ozone generator fed into multiple sterilization chambers controlled by the controller. One smaller and less expensive vacuum pump and ozone generator may be sufficient to sterilize large amounts of medical equipment present in the total assembly of chambers. The controller may run sterilization programs in parallel fully or overlapping partially in time. Control valves governing flow passage of air, steam and ozone in and out of the chambers are also controlled by the controller.

12 Claims, 5 Drawing Sheets

CONTROL SYSTEM FOR OZONE STERILIZATION IN MULTIPLE COMPACT CHAMBERS

FIELD AND BACKGROUND OF THE INVENTION

The present invention generally relates to apparatus and methods for ozone ($O_3$) sterilization of medical equipment and more particularly, to apparatus and methods for ozone sterilization of medical equipment using a centralized controller and other devices to control and perform sterilization of the instruments housed in multiple chambers, each of relatively compact size.

Ozone sterilization of medical equipment is typically performed by preparing the medical equipment with water vapor, which increases the effectiveness of a later exposure to ozone. To improve the effectiveness and shorten the time of the ozone sterilization, each step of the process is preceded by removing the internal atmosphere in the sterilization chamber by creating a vacuum inside the chamber thus ensuring the penetration of the next step's atmosphere into and around the medical equipment to be sterilized. Accordingly, an ozone sterilization cycle requires removing the air from the chamber, pumping steam into the chamber, pumping ozone into the chamber, allowing the sterilization process to run its course and then pumping out the contents of the chamber before pumping in clean air.

Accordingly, the process requires, among other things, a chamber large enough to house the medical instruments, an ozone generator (ozonator) strong enough to generate ozone for the large chamber, and a pump for air removal strong enough for the large chamber. Larger chambers, for example a 100 liter chamber, require larger peripheral service devices. The larger peripheral service devices (e.g. pumps and ozonators) tend to be not just larger in size but also more sophisticated and hence significantly more expensive. In addition, production costs for producing the larger chambers rise faster than linearly in proportional to the size of the chamber.

Medical equipment comes in many shapes and sizes, including long tubular instruments such as catheters and endoscopes. Different medical instruments, based on their structure and type of material, require different sterilization programs. For example, hollow, elongated medical instruments closed on one end may require repetition of a vacuum, steam, and ozone cycle one or more times to ensure proper penetration of ozone throughout the depth of the inside of the medical instrument, including in hard to access areas.

The typical overall time for ozone sterilization is 20-30 minutes. Accordingly, since some instruments require cycle repetition, the pump may have to achieve a required level (i.e. 3 to 6 millibars) in less than 5 minutes and preferably 3 minutes. In addition, the time to introduce ozone into the chamber may have to be 3 minutes or less to leave enough time for the entire sterilization cycle.

There is an ongoing need for improved methods and devices for ozone sterilization that are cost effective, efficient and suitable for all types of medical equipment.

SUMMARY OF THE PRESENT INVENTION

One aspect of the present invention is an apparatus for sterilizing instruments, comprising a plurality of sterilization chambers, each sterilization chamber having a volume of approximately thirty liters or less, each sterilization chamber for sterilizing instruments and having an ozone inlet controlled by a ozone control valve, a steam inlet controlled by a steam control valve, an outlet conduit controlled by a vacuum control valve and a clean air inlet controlled by an air control valve; a vacuum pump having a conduit to the vacuum control valve of each of the sterilization chambers in the plurality, the vacuum pump strong enough to pump out a gaseous contents of a sterilization chamber to six millibars of pressure in less than five minutes only if the sterilization chamber has a volume of approximately thirty liters or less; an ozone generator having a conduit to the ozone control valve of each of the sterilization chambers in the plurality such that the ozone generator can inject ozone into any of the sterilization chambers; a steam generator having a conduit to the steam control valve of each of the sterilization chambers in the plurality so that the steam generator can inject steam into any of the sterilization chambers; and a controller for independently controlling the vacuum pump, the vacuum control valves, the ozone generator, the ozone control valves, the steam generator, the steam control valves, and the clean air control valves so as to operate independent sterilization programs in each sterilization chamber.

A further aspect of the present invention is a method of sterilizing instruments, comprising (a) forming conduits between a sterilization chamber and a pump, between the sterilization chamber and an ozone generator, between the sterilization chamber and a steam generator and between the sterilization chamber and a source of ambient air, each conduit controlled by a control valve; (b) repeating step "(a)" for one or more additional sterilization chambers using the same pump and ozone generator; (c) housing the instruments in the sterilization chambers by grouping instruments requiring a same sterilization program in a same sterilization chamber, subject to a size limitation of the same sterilization chamber, wherein the sterilization program required depends on a structure and material of the instruments; (d) using a controller to control operation of the control valves, the pump, the ozone generator and the steam generator to conduct separate sterilization programs for each sterilization chamber such that at least one step of one sterilization program overlaps in time with a second sterilization program, wherein each sterilization program includes at least one instance of the following five steps: vacuuming out contents of a sterilization chamber, injecting steam into the sterilization chamber, injecting ozone into the sterilization chamber, allowing sterilization to occur and re-filling the sterilization chamber with clean air.

A still further aspect of the present invention is directed to an apparatus for sterilizing instruments, comprising three or more sterilization chambers of approximately 30 liter volume or less, each sterilization chamber for sterilizing instruments and having an ozone inlet controlled by an ozone control valve, a steam inlet controlled by a steam control valve, an outlet valve controlled by a vacuum control valve and a clean air inlet controlled by an air control valve; a vacuum pump having a conduit to the vacuum control valve of each of the three or more sterilization chambers, the vacuum pump only strong enough to pump out a gaseous contents of a sterilization chamber of up to approximately 30 liters to six millibars of pressure in less than five minutes; an ozone generator having a conduit to the ozone control valve of each of the three or more sterilization chambers, the ozone generator only strong enough to generate and inject ozone in less than five minutes into sterilization chambers having volumes of not more than approximately 30 liters sufficient to reach an ozone concentration of 12% by weight; a steam generator having a conduit to the steam control valve of each of the three or more sterilization chambers; and a controller for receipt of instructions to run sterilization programs in particular sterilization chambers, the controller programmed to operate parallel sterilization programs in the three or more sterilization chambers utilizing the pump, ozone generator, steam generator, vacuum control valves, ozone control valves, steam control valves and air control valves so as to either pump out gaseous contents of the particular sterilization chamber, inject steam or ozone or clean air into the particular sterilization chamber or place the particular sterilization chamber in a holding pattern for sterilization to occur.

These and other features, aspects and advantages of the present invention will become better understood with reference to the following drawings, descriptions and claims.

BRIEF DESCRIPTION OF THE DRAWINGS

Various embodiments are herein described, by way of example only, with reference to the accompanying drawings, wherein.

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

The present invention generally provides a method and apparatus for sterilizing medical instruments in sterilization chambers using ozone. Multiple relatively small sterilization chambers may each be connected to a single vacuum pump, a single ozone generator and a single steam generator. Each sterilization chamber may have a separate control valve for each connection to each device (i.e. pump, ozone generator etc.). The ozone generator and the vacuum pump may be designed to be suitable for engagement with the relatively small sterilization chambers. A controller controls operation of the control valves and thereby controls operation of the vacuum pump, ozone generator and steam generator, thereby running sterilization programs that may be tailored for each sterilization chamber. The sterilization programs for the different chambers may overlap in time.

In contrast to the prior art apparatuses for sterilization of medical instruments, in which a large sterilization chamber of 60 or 100 liters is used to sterilize all medical instruments, the sterilization apparatus of the present invention may utilize multiple smaller sterilization chambers of approximately 30 liters. As a result, one smaller and less expensive vacuum pump and one smaller and less expensive ozone generator may be sufficient to sterilize large amounts of medical equipment present in the total assembly of chambers. In further contrast to the prior art sterilization apparatuses, which use a relatively large amount of power for a given volume (of 60 liters or more) because for each sterilization chamber there is a separate pump, ozone generator and steam generator, the sterilization apparatus of the present invention may use less power for the same total volume by maintaining the number of ozone generators, pumps and steam generators at one, even when the number of chambers increases. In further contrast to the prior art sterilization apparatuses, which are more expensive to operate since they rely on more sophisticated and more expensive ozone generators and vacuum pumps to inject or empty the large sterilization chambers, the apparatus of the present invention may save significant cost by utilizing small chambers and small, less sophisticated and less expensive ozone generators and pumps to inject and empty such chambers. In addition, the production cost for manufacturing larger sterilization chambers increases more than linearly. In addition, it is easier to achieve uniform acceptable levels of ozone concentration throughout the chamber when pumping ozone into smaller chambers. In still further contrast to the prior art sterilization methods, which may waste energy by using the same large volume chamber for sterilization regardless of the volume of instruments to be sterilized, the method and apparatus of the present invention may be energy efficient and environmentally friendly by being much more able to vary the number of sterilization chambers in actual use in proportion to the total volume of medical instruments to be sterilized. In further contrast to the prior art sterilization apparatuses, in which there is a considerable lead time and a considerable tail time at the beginning and end of the sterilization process, in the method and apparatus of the present invention the lead time and tail time may be significantly reduced. In still further contrast to the prior art sterilization apparatuses and methods, which may lump all medical instruments into a single large chamber, the apparatus of the present invention may operate separate sterilization programs custom tailored to each type of medical instrument requiring a separate cycle of pumping and ozone generation. For example, endoscopes and catheters, because they are long and tubular, may require repetition of a cycle of vacuum pumping and injecting of steam and ozone to achieve an effective sterilization. This may make the apparatus of the present invention much more flexible and convenient to use. If after a sterilization cycle starts further medical instruments need to be sterilized, the apparatus of the present invention can just add them to a further small sterilization chamber and set the controller to apply the needed sterilization program without having to either stop the ongoing cycle or wait for the end of the sterilization cycle currently operating. Furthermore, in the prior art, the most problematic instrument may dictate the type of sterilization program utilized for all instruments since it is necessary to be sensitive to the requirements of that one problematic instrument. For example, if you have a long tube, all instruments placed in the one large chamber will undergo the program for that one long tube. In the present invention, one small chamber may be used to sterilize the long tube and the remaining instruments may be subjected to the regular sterilization program. In further contrast to the prior art, the sterilization chambers of the present invention may be specially designed to host oddly shaped instruments. In still further contrast to the prior art, in which sterilization programs are run in series, the sterilization programs of the present invention may run in parallel, or at least overlapping in time.

The principles and operation of an apparatus and method for sterilization of medical instruments according to the present invention may be better understood with reference to the drawings and the accompanying description.

Figure 1:
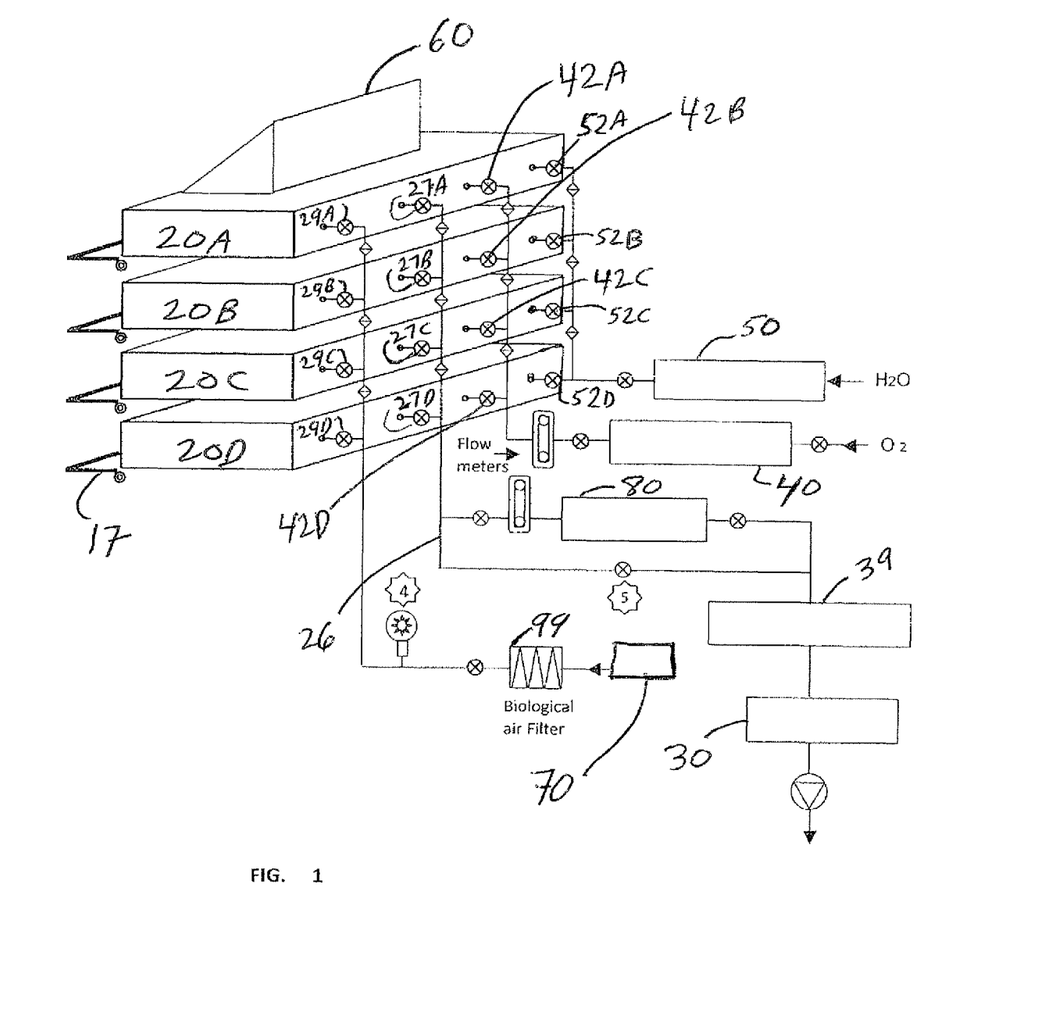
FIG. 1 is a schematic showing a sterilization apparatus in accordance with one embodiment of the present invention.

As seen in FIG. 1, apparatus 10 for sterilizing medical instruments, may comprise a plurality of sterilization chambers 20, for example sterilization chambers 20A, 20B, 20C, 20D, etc. The number of sterilization chambers may vary and may consist of two, three, four or more. Two or three or four may be preferable in some contexts. Sterilization chambers 20A, 20B, 20C, 20D may or may not be identical to one another. Apparatus 10 may be designed to be modular so that additional chambers may be added to, for example, an existing three-chamber apparatus to make it into a four-chamber apparatus.

Figure 2:
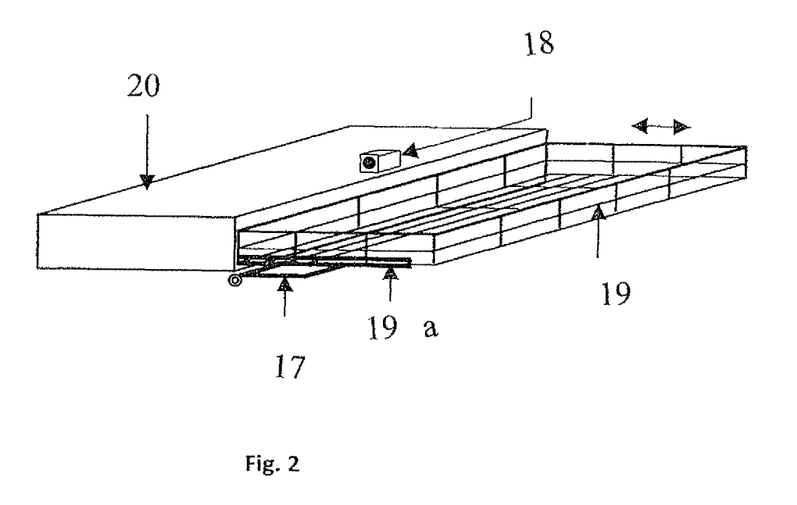
FIG. 2 is an isometric view of a sterilization chamber used in the apparatus of FIG. 1 including a movable drawer in accordance with one embodiment of the present invention.

FIG. 2 illustrates how medical instruments may be placed into a particular sterilization chamber 20. As is shown in FIG. 2, a sliding drawer 19 of chamber 20 may open and close with the aid of a sliding device 19a and may be used to store and hold medical instruments (not shown) during sterilization. Sterilization chamber 20 may also have associated with it a door 17 controlled by a door locking mechanism 18.

Each sterilization chamber 20A, 20B, 20C, 20D may be designed for sterilizing medical instruments using ozone. In fact, although sterilization chambers 20A, 20B, 20C, 20D may be identical, they may be used to house medical instruments that may be grouped in accordance with their structure and type of material, i.e. in accordance with the particular sterilization program that is required for them based on their structure and material. Some medical instruments require different sterilization programs than others. For example, some medical instruments may have a long narrow shape which may make it difficult for ozone to access and sterilize hard to reach portions of the inside of the instrument. This may make it take longer for such instruments to be sterilized. Accordingly, different medical instruments should ideally be grouped together with those other medical instruments that share the same required sterilization program. In accordance with the present invention, the medical instruments may be grouped together based on the kind of sterilization program they need.

This grouping of medical instruments together based on their required sterilization program may naturally be subject to a caveat based on a size limitation of the sterilization chamber. A single chamber may be unable to accommodate all medical instruments requiring a particular sterilization program. In that case, a second sterilization chamber may be needed. Depending on the number of available sterilization chambers to fit the number of medical instruments requiring a particular sterilization program, it may be necessary to house instruments requiring this program in other sterilization chambers being utilized primarily for other sterilization programs. While the objective may be to maximize, where possible, grouping together of instruments requiring similar sterilization programs with other instruments requiring similar programs, one need not foreclose the possibility of housing some medical instruments requiring a first type of sterilization program in sterilization chambers being utilized primarily for a different sterilization program.

As seen in FIG. 1, each sterilization chamber 20A, 20B, 20C, 20D may be operated independently of one another and may be connected to an ozone inlet conduit 41A, 41B, 41C, 41D controlled by a ozone control valve 42A, 42B, 42C, 42D, a steam inlet conduit 51A, 51B, 51C, 51D controlled by a steam control valve 52A, 52B, 52C, 52D, a (vacuum) outlet conduit 26 controlled by a vacuum control valve 27A, 27B, 27C, 27D and a clean air inlet 28A, 28B, 28C, 28D controlled by an air control valve 29A, 29B, 29C, 29D. Although other configurations may be envisioned, in FIG. 1, each of these control valves 42A, 42B, 42C, 42D, 52A, 5213, 52C, 52D, 27A, 2713, 27C, 27D, 29A, 2913, 29C, 29D may be situated adjacent a rear of sterilization chambers 20A, 20B, 20C, 20D respectively.

Apparatus 10 may also include a vacuum pump 30 having a conduit 26 to the vacuum control valve 27A, 27B, 27C, 27D of each of the sterilization chambers 20A, 20B, 20C, 20D. As seen in FIG. 1, an ozone destruct unit 39 may be placed upstream of vacuum pump 30 in order to destroy the ozone prior to the entry of the gaseous contents of the chamber 20 into vacuum pump 30. Vacuum pump 30 may be capable of pumping out the gaseous contents of any one of the sterilization chambers 20A, 2013, 20C, 20D to reach a pressure level measured at between 3 to 6 millibars in less than five minutes. The gaseous contents may comprise air, a combination of air and ozone, a combination of air, ozone and steam or it may comprise other gases. When referring to the capacity of a device to lower pressure levels to between 3 to 6 millibars, where discrete pressure levels rather than a range of pressure levels is required, the pressure level of "6 millibars" has been used herein.

Since an overall sterilization program may typically last twenty to thirty minutes in total, vacuum pump 30 may be suitable for and designed to be used to pump out the gaseous contents of a sterilization chamber having a relatively small volume of approximately (e.g. plus or minus 15%) 30 liters or less to reach 3 to 6 millibars of pressure in less than 5 minutes and more preferably in approximately 3 minutes. To accomplish this, vacuum pump 30 may be a prior art vacuum pump. For example a vacuum pump manufactured by Edwards Limited (see www.edwardsvacuum.com) having product number "XD5" may be operatively engaged to a sterilization chamber 20 having dimensions of 15 centimeters (cm) by 30 cm by 60 cm, i.e. having a volume capacity of approximately 27 liters. Pumping at 97 liters per minute, or 5.8 cubic meters per hour, it would take an Edwards XD5 vacuum pump approximately 2.8 minutes to pump out the gaseous contents of a 27 liter sterilization chamber 20 to reach 3 to 6 millibars of pressure. Such an Edwards XD5 vacuum pump may be suitable for and designed to be used to pump out the gaseous contents of a 27-liter sterilization chamber. This is in contrast to the larger type vacuum pumps that are strong enough and are designed to pump out the gaseous contents of 100-liter chambers or 60-liter chambers. Furthermore, it is estimated that the Edwards XD5 vacuum pump may take approximately 12 minutes to pump out the to gaseous contents of a 100-liter sterilization chamber of the prior art.

Pump 20 may be a vacuum pump that is only strong enough to pump out the gaseous contents of sterilization chambers of up to approximately 30 liters to 6 millibars of pressure in less than five minutes and such pump 30 may be unable to pump out the gaseous contents of sterilization chambers of larger volume to 6 millibars of pressure in less than 5 minutes. This allows utilization of smaller less sophisticated and less expensive vacuum pumps in the sterilization apparatus 10 to sterilize large total amounts of medical equipment present in the sum total of all the sterilization chambers 20.

Apparatus 10 may also include an ozone generator 40 having a conduit 41 to the ozone control valve 42A, 42B, 42C, 42D of each of the sterilization chambers 20A, 20B, 20C, 20D in the plurality of chambers such that ozone generator 40 may be able to inject ozone into any of the sterilization chambers. Ozone generator 40 may have oxygen ($O_2$) as an input to generate ozone. Ozone generator 40 may be designed to generate and pump ozone into a sterilization chamber 20 of approximately 30 liters or less in less than three minutes. To accomplish this, prior art ozone generators designed for sterilization chambers of approximately 30 liters or less may be utilized. For example, an ozone generator called "Atlas 100" manufactured by a company called. Absolute Ozone may be able to generate ozone at up to 100 grams per hour yielding a best concentration of up to 12% ozone in the sterilization chamber, as measured by dividing the weight of the ozone by the weight of the oxygen. Utilizing a working pressure of 1000 millibar would take approximately 1.4 minutes to reach an ozone concentration of 12% by weight in a 27-liter sterilization chamber (15 cm by 30 cm by 60 cm). In contrast, for a 100-liter sterilization chamber, it would take approximately 5 to 6 minutes to reach 12% by weight ozone concentration in the sterilization chamber starting with a working pressure of 1000 millibars. Since the sterilization program is estimated to typically take 20-30 minutes, and since as seen from FIGS. 3-5, most sterilization programs require repetition of steps, the Atlas 100 and other ozone generator designed for compact chambers would not be suitable for generating and injecting ozone into a 100-liter sterilization chamber. Ozone generator 40 may be designed for injecting ozone into sterilization chambers having volumes of approximately 30 liters or less (i.e. not more than approximately 30 liters where "approximately" means plus or minus 15%) within approximately 3 minutes, which means ozone generator 40 may be capable of generating and injecting enough ozone to fill the 30 or fewer liter chamber with ozone in accordance with proper sterilization procedure for medical instruments within approximately 3 minutes or under 5 minutes and may be incapable of doing the same with a larger volume container in similar time periods. Consequently, smaller less sophisticated and cheaper devices can be used to sterilize large total amounts of medical equipment present in the sum total of all the chambers.

Apparatus 10 may also include a steam generator 50 that generates steam from water inputted into it. Steam generator 50 may be connected by a conduit 51 controlled by a steam control valve 52A, 5213, 52C, 52D to each of the sterilization chambers 20A, 20B, 20C, 20D in apparatus 10 so that steam generator 50 can inject steam into any of the sterilization chambers 20A, 20B, 20C, 20D as directed by controller 60. Steam generator 50 may be designed for generating and injecting steam into sterilization chambers of approximately 30 liters or less. Steam generator 50 may be of the type that would not efficiently generate steam into a 100 liter sterilization chamber, for example, in an amount of time useful for completing the sterilization program in 20-30 minutes.

Each sterilization chamber 20A, 20B, 20C, 20D may also be connected to a source 70 of ambient air through an air control inlet 28A, 28B, 28C, 28D controlled by air control valve 29A, 29B, 29C, 29D. For example, sterilization chamber 29C may have air control valve 29C adjacent chamber 29C and between chamber 29C and an air inlet 28C that may lead to a source 70 of ambient air. A biological air filter 99 may be used to ensure that re-filling chambers 20 with clean air does not re-introduce unacceptable levels of bacteria.

Figure 5:
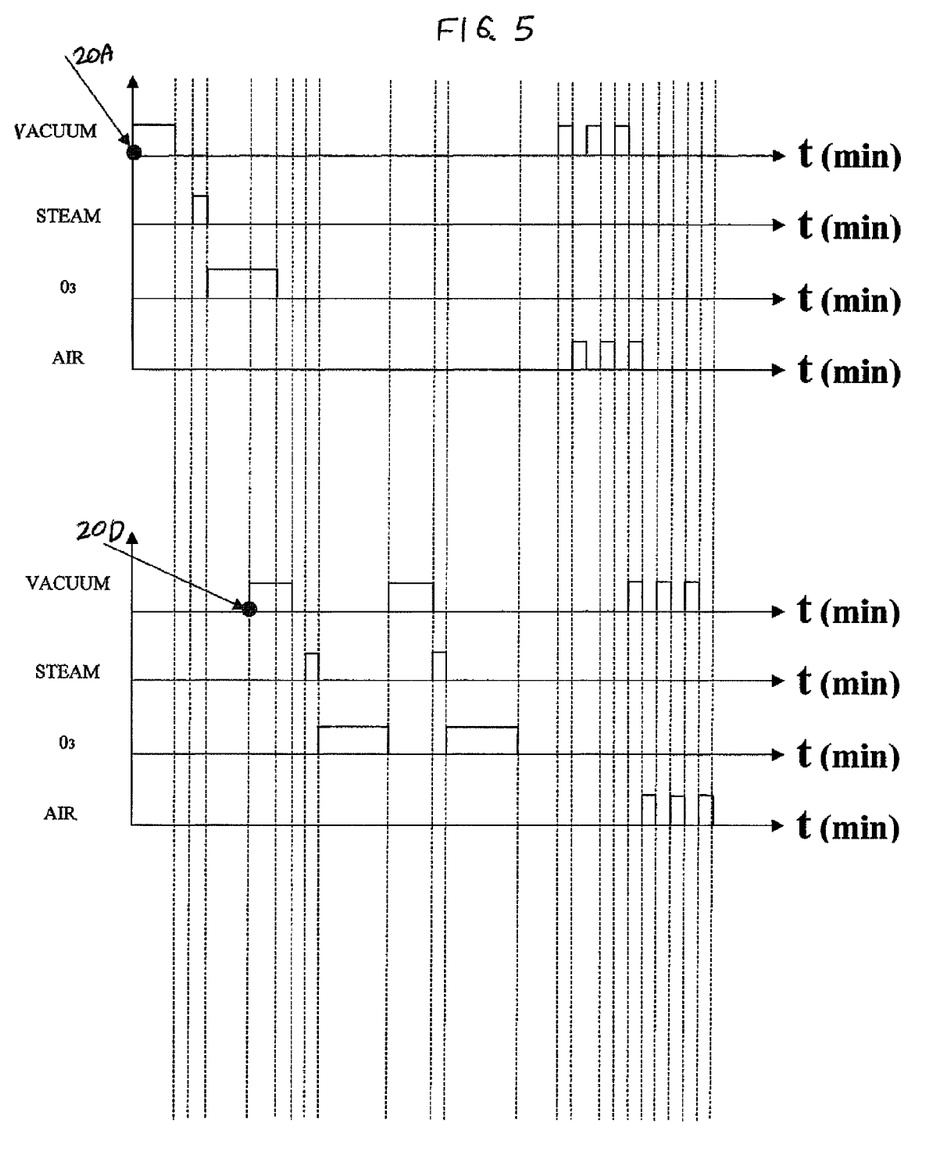
FIG. 5 is a graph showing an apparatus of the present invention operating two overlapping sterilization programs in parallel in accordance with one embodiment of the present invention.

As seen from FIG. 5, after the sterilization program is completed a particular sterilization chamber, for example sterilization chamber 20B, may be allowed to access a source 70 of ambient air through an inlet 28B by opening air control valve 2913. However, as also seen from FIG. 5, multiple instances of access to clean air punctuated by multiple instances of evacuation of the gaseous contents of the chamber 20B may be necessary to ensure thorough access of the clean air into the sterilization chamber 20B.

Figure 3:
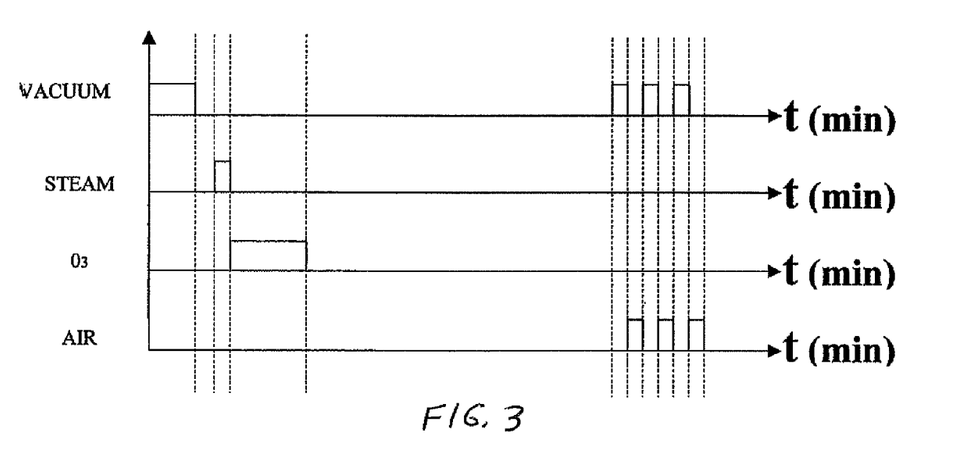
FIG. 3 is a graph of a sterilization program for relatively easy to sterilize medical instruments.
Figure 4:
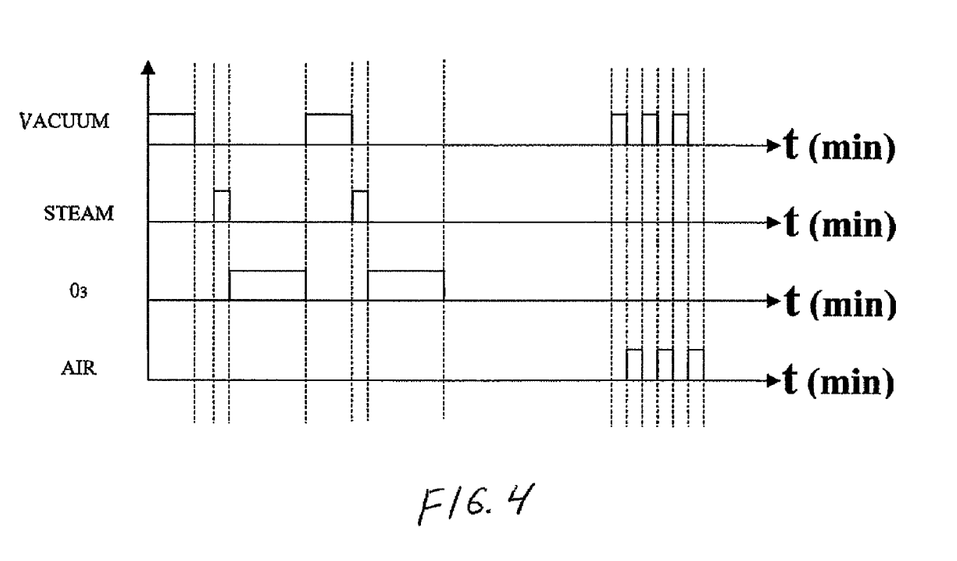
FIG. 4 is a graph of a sterilization program for long tubular medical instruments that are relatively harder to sterilize.

FIGS. 3 and 4 each depicts a graph of a sterilization program for a single sterilization chamber taken alone, but for different kinds of medical instruments. FIGS. 3 and 4 also utilize multiple instances of clean air distribution alternating with multiple instances of pumping out the gaseous contents of the sterilization chamber at the end of the program.

Apparatus 10 may include a common controller 60 for controlling vacuum pump 30, the vacuum control valves, ozone generator 40, the ozone control valves, steam generator 50, the steam control valves, and the clean air control valves. Controller 60, which may be or may include a microprocessor, may be connected electronically to pump 30, ozone generator 40, steam generator 50 and all control valves as well as to other portions of apparatus 10, such as a drawer 19 or a user-controlled button (not shown). Controller 60 may receive instructions to run sterilization programs in particular sterilization chambers in parallel. For example, a user may push a button (not shown) on apparatus to indicate the user wishes to run a sterilization program in sterilization chamber 20A. Alternatively, the closing of the drawer 19 may itself signal controller 60 to implement a sterilization program in that chamber 20B for example.

Controller 60 may be programmed to operate sterilization programs in parallel or partially parallel in the plurality of sterilization chambers utilizing the pump, ozone generator, steam generator, vacuum control valves, ozone control valves, steam control valves and air control valves. Controller 60 may therefore direct pump 30 to pump out gaseous contents of sterilization chamber 20A at a time, or overlapping with a time, that controller 60 has directed ozone generator 40 to inject ozone into sterilization chamber 20B. This may also be at a time, or overlapping with a time, that controller 60 has directed steam generator 50 to inject steam into sterilization chamber 20C. Controller 60 may also direct the appropriate air control valve (29A, 29B, 29C, or 29D) to allow clean air into the particular sterilization chamber at a time, or overlapping with a time, that controller 60 has directed pump 30 to pump contents out of another chamber 20 or has directed ozone generator 50 to pump steam into another chamber 20. In addition, controller 60 may control the pump 30, ozone generator 40, steam generator 50 and all control valves such as to place a particular sterilization chamber in a holding pattern so that sterilization to occur. This means that ozone, steam and air are not being injected or pumped out of the particular sterilization chamber.

Controller 60 may also be programmed to calculate the availability of several devices, including the vacuum pump, the ozone generator and the steam generator for operative engagement to particular sterilization chambers 20A, 20B, 20C, 20D of the two, three or four or more sterilization chambers and to use one or more of those availabilities to operate the vacuum pump, ozone generator and steam generator in the sterilization programs.

Although FIG. 1 does not specifically delineate the electrical or other communication connections between controller 60 and the various other components of apparatus 10, it should be understood that controller 60 may be connected to pump 30, ozone generator 40, steam generator 50, ozone meter 80, ozone destructor 39, a source of ambient air 70 and all of the control valves mentioned in this patent application. This does not preclude versions in which fewer than all of the above are connected to the controller 60. Furthermore, whenever it is stated that a device or component is connected to sterilization chambers 20A, 20B, 20C, 20D, it should be understood that the listing of these four chambers is merely illustrative of the list of the sterilization chambers 20 in apparatus 10, however many there may be in apparatus 20, and that the device or component may therefore be connected to fewer or more than four sterilization chambers.

There may be a concern of ozone leakage from a sterilization chamber 20 even though apparatus 10 may be operating at sub-atmospheric pressure. Furthermore, sterilization of medical instruments may have to meet regulatory standards. Accordingly, apparatus 10 may further include an ozone meter 80 that checks the ozone concentration. Ozone meter 80 may issue a warning when the ozone level in a particular sterilization chamber 20A, 203, 20C, 20D has either not increased sufficiently to implement an effective sterilization or has declined to a certain level, for example due to leakage.

FIG. 5 is a graph showing apparatus 10 operating two sterilization programs overlapping in time in accordance with one embodiment of the present invention. An arrow ending in a point is used to designate the point in time at which the sterilization program for a particular sterilization chamber (20A, 20D) has begun. Although two sterilization chambers, for example 20A, 20D, may be used to operate the two sterilization programs, sterilization chambers 20A, 20D may rely on a single pump 40, a single ozone generator 50 and a single steam generator 60, all governed by a common controller 60.

The present invention may also be characterized as a method 100 of sterilizing medical instruments. As seen from FIG. 6, method 100 may be comprised of a step 110 involving forming conduits between a sterilization chamber 20 and a pump 30, between the sterilization chamber 20 and an ozone generator 40, between the sterilization chamber and a steam generator 50 and between the sterilization chamber 20 and a source 70 of ambient air. Each conduit may be controlled by a control valve.

Figure 6:
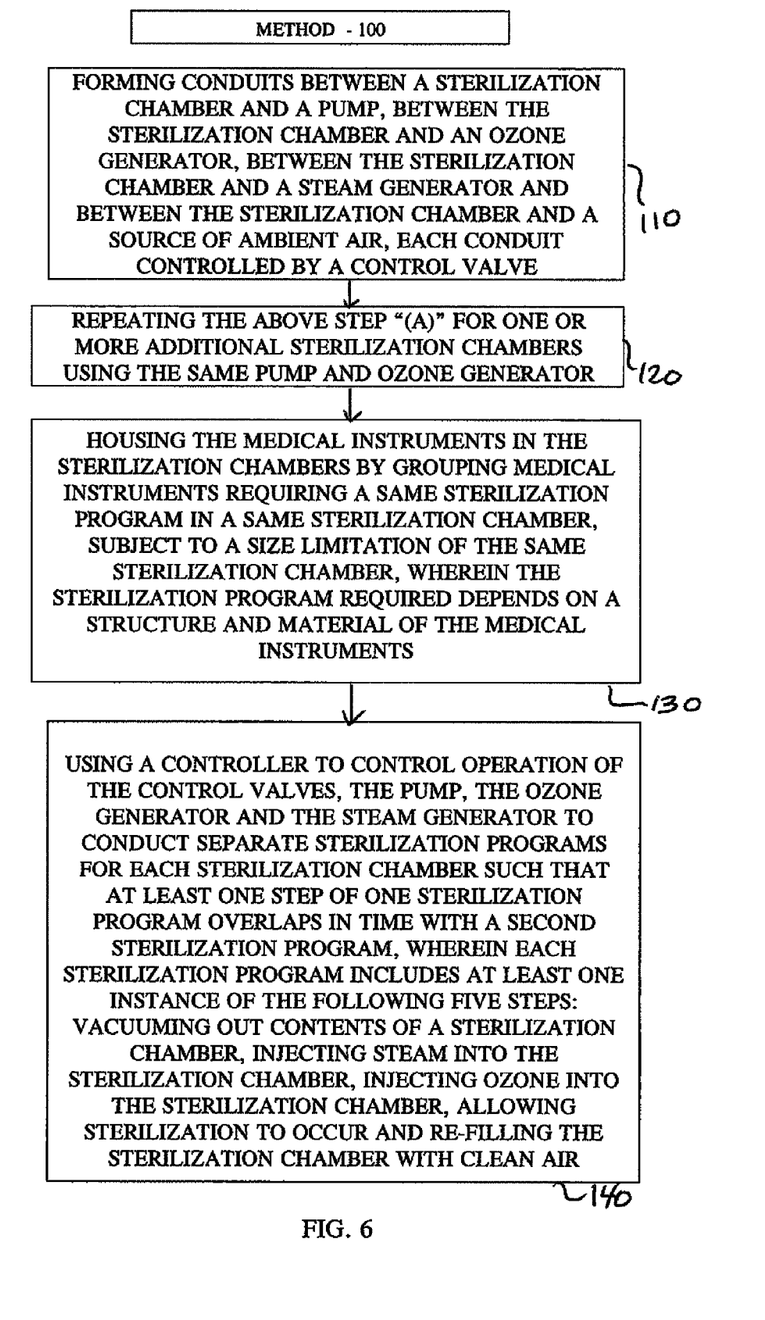
FIG. 6 is a flow chart showing a method in accordance with one embodiment of the present invention.

A further step 120 may involve repeating the above step "(a)" for one or more additional sterilization chambers using the same pump 30 and ozone generator 40. Further, the same steam generator 50 may also be utilized. The same source 70 of ambient air may also be utilized. The repetition in step 120 of forming conduits between additional sterilization chambers and the common vacuum pump 30, ozone generator 40, steam generator 50 or source 70 of clean air is not intended to limit, in any way, the configuration or other characteristics of the conduits, for example as between parallel connections to the pump/ozone generator/steam generator/clean air versus a branch off a common line. The conduits may assume any appropriate configuration.

In a still further step 130, the medical instruments to be sterilized may be placed into and stored in the sterilization chambers 20A, 20B, 20C, 20D by grouping medical instruments requiring a same sterilization program in a same sterilization chamber, subject to a size limitation of the same sterilization chamber. In order to accomplish this grouping, note may be taken of how a structure and material of the medical instruments may demand a particular sterilization program.

Step 140 of method 100 may comprise using a controller 60 to control operation of the control valves, the pump, the ozone generator and the steam generator to conduct separate sterilization programs for each sterilization chamber such that at least one step of one sterilization program overlaps in time with a second sterilization program. In some cases, two or three or more of the steps of the first sterilization program may overlap and be running in parallel with the second or a third or further sterilization program.

Each sterilization program may include at least one instance of the following five steps: vacuuming out contents of a sterilization chamber, injecting steam into the sterilization chamber, injecting ozone into the sterilization chamber, a waiting period during which sterilization is allowed to occur and re-filling the sterilization chamber with clean air. Controller 60 may operate the separate sterilization programs by controlling the pump, the ozone generator, the steam generator and the control valves so as to carry out permutations of the five steps. Each injecting of ozone into a sterilization chamber may be accomplished in three minutes or less. Each vacuuming out of contents of a sterilization chamber may be accomplished in five minutes or less.

As seen in the upper portion of FIG. 5, a first sterilization program may involve vacuuming out contents of a sterilization chamber, injecting steam into the sterilization chamber, injecting ozone into the sterilization chamber, allowing sterilization to occur. This may be followed by a subsequent series of alternating steps of (i) vacuuming out contents of the sterilization chamber and (ii) re-filling the sterilization chamber with clean air. When vacuuming out the ozone, the ozone may be pumped through an ozone destructor 39 that converts the ozone back to oxygen or to another environmentally friendly gas. Prior to each instance of re-filling the sterilization chamber with clean air, the ozone level may be monitored. As seen in the lower portion of FIG. 5, a second sterilization program may involve (i) vacuuming out contents of a sterilization chamber, (ii) injecting steam into the sterilization chamber, (iii) injecting ozone into the sterilization chamber, (iv) repeating steps (i) through (iii) and (v) a waiting period during which sterilization is allowed to occur. The second sterilization program may also involve a subsequent series of alternating steps of (i) vacuuming out contents of the sterilization chamber and (ii) re-filling the sterilization chamber with clean air. When vacuuming out the ozone, the ozone may be pumped through an ozone destructor 39 that converts the ozone back to oxygen or to another environmentally friendly gas. Prior to each instance of re-filling the sterilization chamber with clean air, the ozone level may be monitored.

It can readily be appreciated that using the method and apparatus of the present invention, if an urgent need to sterilization some medical instruments becomes apparent after a sterilization program has already begun, it would not be necessary to terminate the sterilization program, open the chamber and throw in the additional medical instruments. Nor would it be necessary to wait until the one or more ongoing sterilization programs being operated by controller 60 are completed. The convenience and flexibility of the present invention would permit simply invoking a further sterilization chamber to immediately implement a separate sterilization program for the additional instruments by directing controller 60 to provide the program suited for these particular medical instruments. The same pump 30 and ozone generator 40 can be utilized to accomplish this since they are part of apparatus 10.

It should be appreciated that while the method and apparatus of the present invention has been described in the context of sterilizing medical instruments, it is not limited to such instruments. For example, it may be used for the sterilization of packages provided conformity with applicable rules and regulations is maintained.

While the invention has been described with respect to a limited number of embodiments, it will be appreciated that many variations, modifications and other applications of the invention may be made. Therefore, the claimed invention as recited in the claims that follow is not limited to the embodiments described herein.

What is claimed is:

1. An apparatus for sterilizing instruments, comprising:
a first sterilization chambers, the first sterilization chamber having a volume of approximately thirty liters or less, the first sterilization chamber for sterilizing instruments and having an ozone inlet controlled by a ozone control valve, a steam inlet controlled by a steam control valve, an outlet conduit controlled by a vacuum control valve and a first clean air inlet controlled by a first air control valve, the first clean air inlet for re-filling the first sterilization chamber with clean air;
a second sterilization chamber having a volume of approximately thirty liters or less, for sterilizing instruments, the second sterilization chamber also having an ozone inlet controlled by a ozone control valve, a steam inlet controlled by a steam control valve, an outlet conduit controlled by a vacuum control valve and a second clean air inlet controlled by a second air control valve, the second clean air inlet for re-filling the second sterilization chamber with clean air;

a vacuum pump having a conduit to the vacuum control valve of each of the sterilization chambers in the plurality, the vacuum pump strong enough to pump out a gaseous contents of a sterilization chamber to six millibars of pressure in less than five minutes only if the sterilization chamber has a volume of approximately thirty liters or less;

an ozone generator having a conduit to the ozone control valve of each of the sterilization chambers in the plurality such that the ozone generator can inject ozone into any of the sterilization chambers;

a steam generator having a conduit to the steam control valve of each of the sterilization chambers in the plurality so that the steam generator can inject steam into any of the sterilization chambers; and a controller programmed to independently control the vacuum pump, the vacuum control valves, the ozone generator, the ozone control valves, the steam generator, the steam control valves, and the clean air control valves so as to independently operate the first sterilization programs for sterilizing instruments of a first size and shape in the first sterilization chamber to vacuum out contents of the first sterilization chamber, inject steam into the first sterilization chamber, inject ozone into the first sterilization chamber, allow sterilization to occur and operate a subsequent series of alternating steps of (i) vacuuming out contents of the first sterilization chamber and (ii) re-filling the first sterilization chamber with clean air, the controller also programmed to independently operate the second sterilization program for sterilizing instruments of a second size and shape in the second sterilization chamber to (a) vacuum out contents of the second sterilization chamber, (b) inject steam into the second sterilization chamber, (c) inject ozone into the sterilization chamber, (d) repeat steps "(a)" through "(c)", (e) allow sterilization to occur, and operate a subsequent series of alternating steps of (i) vacuuming out contents of the sterilization chamber and (ii) re-filling the sterilization chamber with clean air.

2. The apparatus of claim 1, further comprising instruments of the first size and shape housed in the first sterilization chamber.

3. The apparatus of claim 1, further comprising instruments of the second size and shape housed in the second sterilization chamber.

4. The apparatus of claim 1, further comprising a third and fourth sterilization chamber, at least one of the third and fourth sterilization chambers are non-identical in structure to at least one of the first and second sterilization chambers.

5. The apparatus of claim 1, wherein at least one but not all of the sterilization chambers has a sliding drawer for housing medical instruments during sterilization of the medical instruments.

6. The apparatus of claim 1, wherein the controller is programmed to operate the first and second sterilization programs such that at least one step of the first sterilization program overlaps in time with the second sterilization program.

7. The apparatus of claim 1, wherein instruments of the first size and shape are instruments that are long and tubular.

8. The apparatus of claim 1, wherein the first sterilization chamber is for sterilizing instruments of the first size and shape and which require the first sterilization program and wherein the second sterilization program is for sterilizing instruments of the second size and shape and which require the second sterilization program.

9. An apparatus for sterilizing instruments, comprising:
three or more sterilization chambers of approximately 30 liter volume or less, including a first sterilization chamber, a second sterilization chamber and a third sterilization chamber, each sterilization chamber having an ozone inlet controlled by an ozone control valve, a steam inlet controlled by a steam control valve, an outlet valve controlled by a vacuum control valve, the first sterilization chamber having a first clean air inlet controlled by a first air control valve, the first clean air inlet for re-filling the first sterilization chamber with clean air, the second sterilization chamber having a second clean air inlet controlled by a second air control valve, the second clean air inlet for re-filling the second sterilization chamber with clean air, the third sterilization chamber having a second clean air inlet controlled by a second air control valve, the second clean air inlet for re-filling the third sterilization chamber with clean air;

a vacuum pump having a conduit to the vacuum control valve of each of the three or more sterilization chambers, the vacuum pump only strong enough to pump out a gaseous contents of a sterilization chamber of up to approximately 30 liters to six millibars of pressure in less than five minutes;

an ozone generator having a conduit to the ozone control valve of each of the three or more sterilization chambers, the ozone generator only strong enough to generate and inject ozone in less than five minutes into sterilization chambers having volumes of not more than approximately 30 liters sufficient to reach an ozone concentration of 12% by weight;

a steam generator having a conduit to the steam control valve of each of the three or more sterilization chambers; and a controller for receipt of instructions to run a first sterilization program to sterilize instruments of a first size and shape in the first sterilization chamber, a second sterilization program to sterilize instruments of a second size and shape in the second sterilization chamber and a third sterilization program to sterilize instruments in the third sterilization chamber, the controller programmed to operate parallel sterilization programs in the three or more sterilization chambers utilizing the pump, ozone generator, steam generator, vacuum control valves, ozone control valves, steam control valves and air control valves so as to either pump out gaseous contents of the particular sterilization chamber, inject steam or ozone or clean air into the particular sterilization chamber or place the particular sterilization chamber in a holding pattern for sterilization to occur, such that at least two steps of the first sterilization program overlap in time with the second or the third sterilization program.

10. The apparatus of claim 9, wherein the controller is programmed to calculate whether an availability of the pump and ozone generator allow immediate implementation of a sterilization program after receiving an instruction to sterilize instruments in a particular sterilization chamber.

11. The apparatus of claim 9, further including an ozone meter for measuring an ozone concentration inside sterilization chambers and for sending a warning when the ozone concentration is insufficient for sterilization.

12. The apparatus of claim 9, the controller programmed to calculate an availability of the vacuum pump, an availability of the ozone generator and an availability of the steam generator for operative engagement to particular sterilization chambers of the three or more sterilization chambers and to use one or more of those availabilities to operate parallel sterilization programs.

* * * * *